United States Patent [19]

Knight

[11] Patent Number: 4,995,873

[45] Date of Patent: Feb. 26, 1991

[54] ABSORBENT GARMENT

[76] Inventor: Jackilyn M. Knight, 30 Tombonda Road, Murwillumbah, New South Wales, Australia, 2484

[21] Appl. No.: 364,764

[22] Filed: Jun. 9, 1989

[51] Int. Cl.⁵ .......................................... A61F 13/15
[52] U.S. Cl. ................................................ 604/391
[58] Field of Search ............... 604/389, 390, 391, 392, 604/393, 394, 395, 396, 385

[56] References Cited

U.S. PATENT DOCUMENTS

| 3,150,664 | 9/1964 | Noel | 604/385 R |
| 3,481,337 | 2/1969 | Ruffo | 604/385.1 |
| 4,051,854 | 10/1977 | Aaron | 604/385 R |
| 4,610,682 | 9/1986 | Kopp | 604/385.1 |
| 4,728,326 | 3/1988 | Gilles | 604/392 |

FOREIGN PATENT DOCUMENTS 2606257  5/1988  France ............................. 604/385.1

Primary Examiner—David J. Isabella
Attorney, Agent, or Firm—Panitch Schwarze Jacobs & Nadel

[57] ABSTRACT

An absorbent garment such as a diaper having a substantially "T"-shaped configuration when laid out flat. The garment can be folded into the shape of a loincloth and is held in place by releasable fastening means such as two component press-on/rip-off adhesive or VELCRO ® strips. It is preferably made from flannelet.

7 Claims, 4 Drawing Sheets

ABSORBENT GARMENT

This invention relates to absorbent garments for containing waste body material. Such garments may be used as diapers for babies and young children and will primarily be described in that content however it will be readily apparent to the skilled addressee that the garments may be suitable for persons of all sizes and ages. In this latter context, the garment will be particularly suitable for persons suffering from incontinence, bowel complaints and the similar afflictions where the uncontrollable release of body fluids is likely to occur.

The traditional diaper comprises a rectangular piece of flannelet which is folded to the desired shape and pinned in place with safety pins. Such diapers require some degree of manual dexterity to properly secure and can be bulky and uncomfortable.

The more recent disposable diaper comes in a wide range of shapes and sizes and is usually fitted with the aid of adhesive strips which are integral with the diaper design. Such diapers are relatively expensive as compared with the traditional non-disposable diaper referred to above, and because of their specific dimensions, come in a range of sizes to fit different sized babies. Thus, it is generally the case that packs of different sizes of disposable diapers must be purchased for families with babies and young children of different ages, and this can be disadvantageous in many instances.

Neither the traditional diaper nor the recent disposable diapers are suitable as general purpose absorbent garments for use by persons of all ages. Furthermore, such diapers cannot always be readily secured by the wearer to the wearer's own body.

It is therefore an object of the present invention to provide an absorbent garment or diaper, which does not have many of the aforementioned disadvantages of traditional diapers and disposable diapers. That is, it is an object of the invention to provide an absorbent garment or diaper which is easy to secure in place, particularly by the user of the garment, which is comfortable to wear, which fits a wide range of sizes, and is relatively inexpensive.

According to the broadest aspect of the present invention, there is provided an absorbent garment having a cross-piece and an intersecting piece which together form a substantially "T"-shaped configuration when the garment is laid out flat, said cross-piece being a relatively narrow band for encircling the lower trunk of the wearer in an overlapping manner and said intersecting piece being a relatively wider and longer band for passing under the crotch of the wearer and looping over the said cross-piece in front of the wearer to produce a loincloth-like arrangement; said garment including releaseable fastening means fitted to the end regions of said intersecting and cross-pieces and to a mid-sectional region of said intersecting piece.

Preferably, the releasable fastening means are two component fasteners, such as hook/loop fasteners, for example, VELCRO® strips, adhesive strips, or the like. VELCRO® strips are preferred.

When VELCRO® strips are used, a hook component strip is suitably fitted each end of the cross-piece on one side, namely, the reverse side, that is, the inner-facing side in use, of the garment, and to the free end of the intersecting piece on the other side, namely, the obverse side of the garment. A mating complimentary component strip is fitted to one end of the cross-piece directly opposed to the hook component strips thereof on the obverse side of the garment and also to the mid-sectional and crotch regions of the intersecting piece on the obverse side of the garment.

The absorbent garment may be a disposable or non-disposable type and may include an outer plastic casing if deemed necessary. It is however, intended primarily to be a non-disposable garment.

Generally, the absorbent garment will be made of flannelet or cotton fabric but any suitable absorbent material can be used. The only requirement here is that the absorbent material have sufficient absorbency for the particular task it has to perform. To this end, several layers of material may be used. Furthermore, an additional layer or layers of the same or different absorbent material may be added in the area or areas in which the greatest amount of absorbency is required. Alternatively, a wadding of cotton, wool or other fibrous material may be sewn between two outer layers of the garment in the required regions. A particularly preferred design is wherein the absorbent garment comprises a double layer of flannelet material having extra layers of flannelet in and around the section which comes in contact with the crotch.

The absorbent garment will preferably be contoured in outline so as to suit the lower body outline of the wearer and so as to ensure that there is no unnecessary bulk or excess material in an area in which it is not required. The function of the cross-piece is suitably enlarged so as to encompass the entire rear lower portion of the trunk of the wearer, and this tapers into a relatively narrow section, which passes under the crotch portion, before once again broadening out to a substantially uniform width over the remaining length of the intersecting piece. This "remaining length" may, however, be further contoured so as to taper towards the bottom or distal end of the intersecting piece and to include a pinched mid-portion where the garment is adapted to be folded back upon itself when in use as described above.

Elastic tape or bands may be included within the peripheral edge regions of the narrow section of the garment which passes under the crotch, in order to ensure a snug fitting of the garment when being worn.

A preferred embodiment of the invention will now be described with reference to the accompanying drawings, in which.

Figure 1:
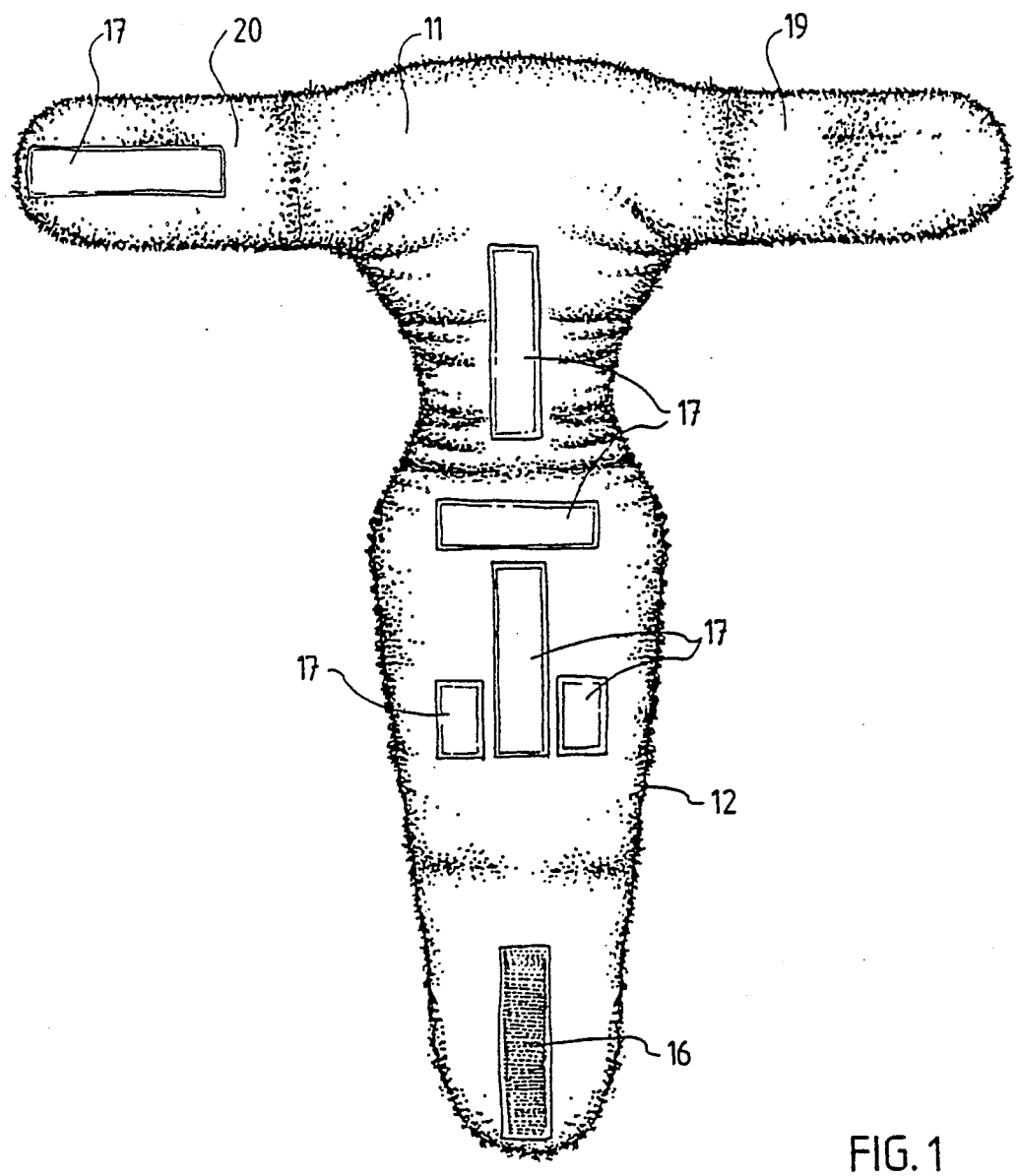
FIG. 1 is a plan view of the obverse side of an absorbent garment according to the present invention when laid out flat.

Referring to the drawings, the absorbent garment comprises a double layer of flannelet material 11, which has been sewn around its perimeter 12 and turned inside out so that the seams are on the interior thereof, thereby producing a neat finish and a smooth edge which will not result in any undue discomfort to the wearer.

The portion of the garment bounded by the single horizontal and two vertical dotted lines 13 (see FIG. 2) includes an extra layer of flannelet which is sewn into the interior of the garment. When the garment is in use, this extra layer extends from the lower rear trunk portion of the person wearing the garment, under the crotch and up the lower front trunk portion. That is, the region shown in the drawings extending from the edge 14 to the fold line 15 of the garment shown in FIG. 5.

Hook VELCRO ® strips 16 are located on the obverse side of the garment cross-piece and on the obverse side of the garment at the distal portion end of the intersecting piece. Complimentary loop strips 17 are located at appropriate positions on the reverse side of the absorbent garment, on one end of the cross-piece and at midpoints along the intersecting piece (see FIG. 1). The VELCRO ® strips may be fitted in position by sewing or by self-adhesion. The VELCRO ® strips are of such a length as to enable a large range of different size persons to use absorbent garments having the same overall dimensions.

Figure 5:
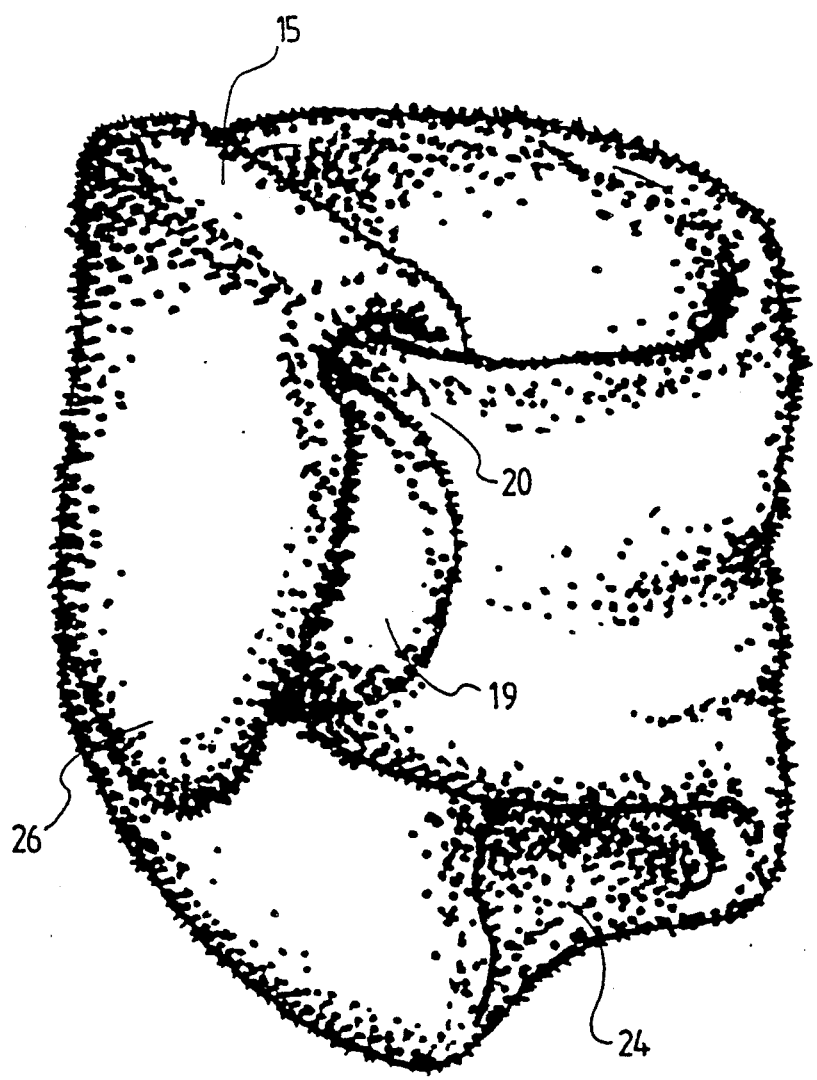
FIG. 5 is a side-on perspective of the fully folded and fastened absorbent garment depicted in the preceding drawings.

The absorbent garment is configured in the form of a "T", with the cross-piece segments 19, 20 of the "T" extending to a sufficient length to girdle the body of the wearer and to overlap one another when fitted as can be seen in FIG. 5.

The junction 21 of the cross-piece and the intersecting piece is expanded in area to cover the lower trunk of the wearer and this then tapers at the crotch area 22 to ensure a comfortable fitting. Elastic tape is sewn in the interior edge portions 23, 24 to ensure that a snug fitting is produced around the limbs of the wearer and to ensure containment of any waste material.

The leg section of the intersecting piece broadens in cross-sectional dimension in the region 25 (see FIG. 1) and then tapers towards its distal end 26.

The distal ends of the cross-piece and the intersecting piece are curved primarily for aesthetic reasons but also to assist in the fitting of the garment.

Figure 2:
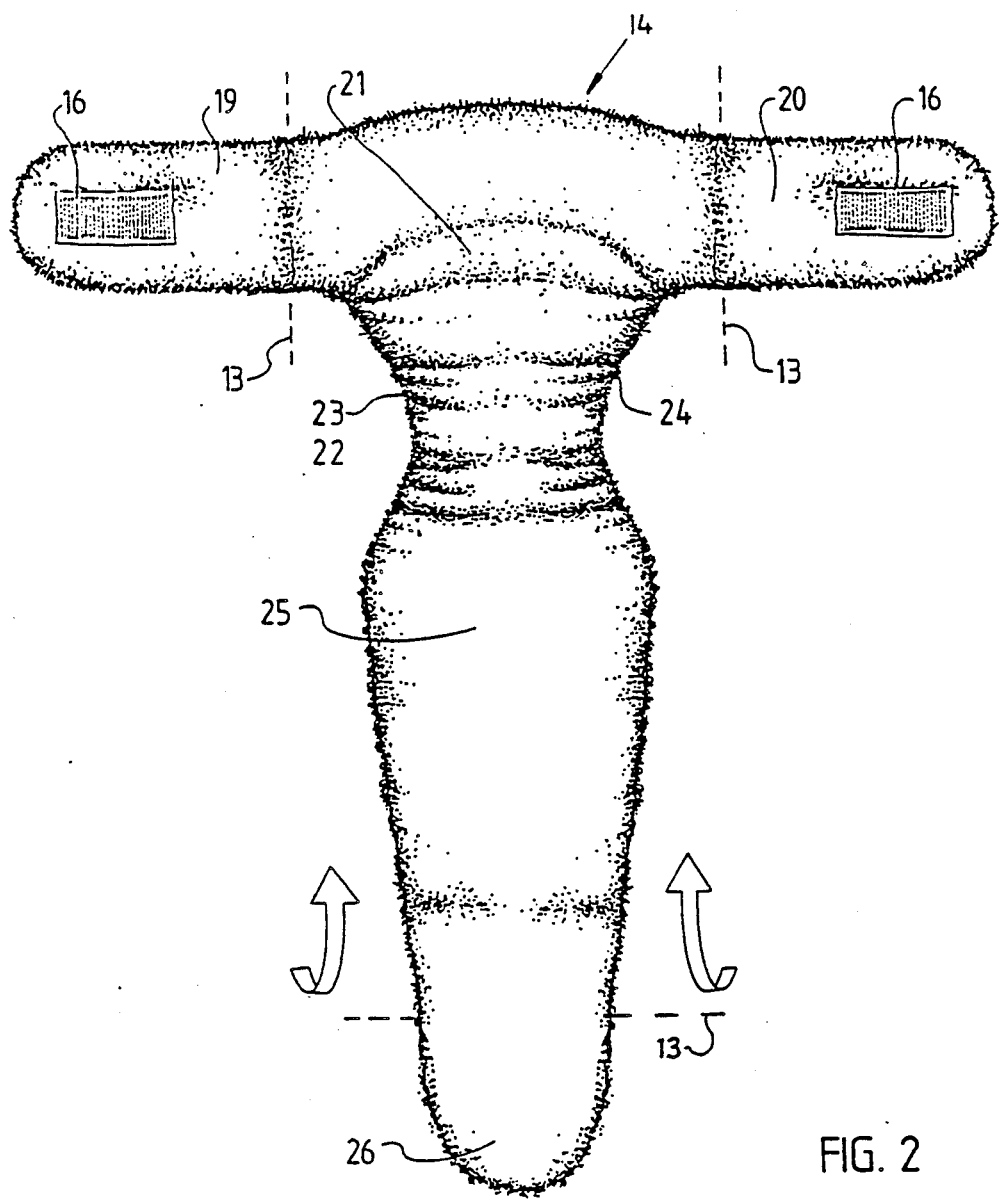
FIG. 2 is a plan view of the reverse side of the absorbent garment depicted in FIG. 1.
Figure 3:
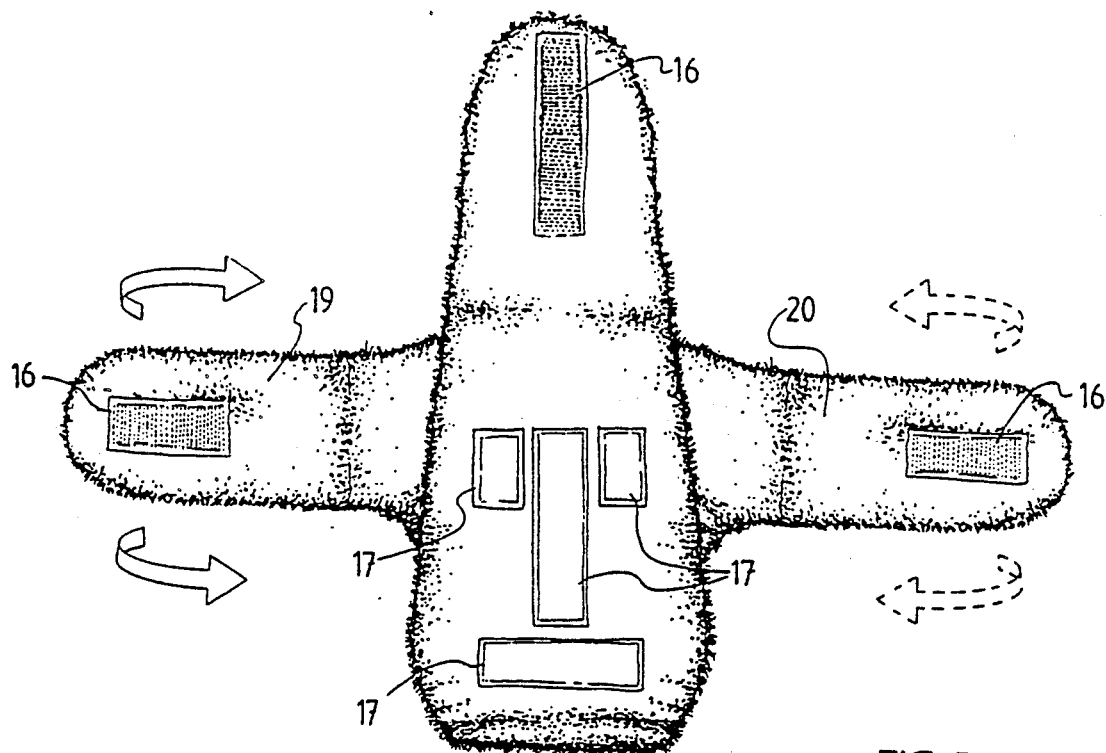
FIG. 3 is a plan view of the partially folded absorbent garment depicted in FIG. 1 and FIG. 2.
Figure 4:
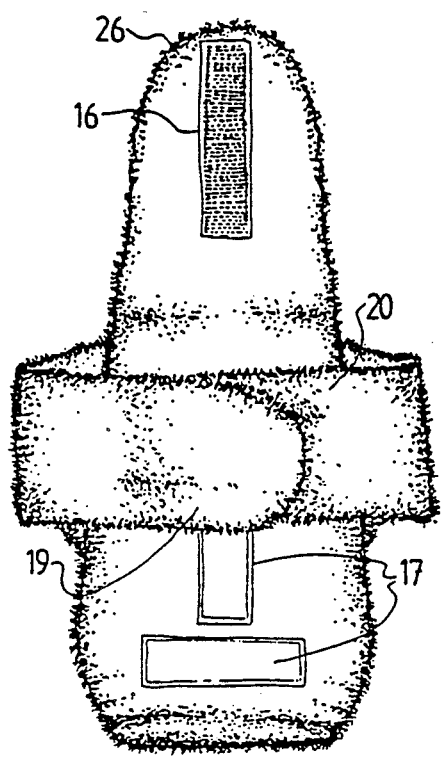
FIG. 4 is a plan view of the next step in folding the absorbent garment depicted in FIG. 3.

To fit the absorbent garment, steps are taken to produce the folds as depicted in FIGS. 3-5. Firstly, the garment is opened out as shown in FIG. 2 and placed against the rear lower section of the wearer's trunk with the cross-piece extending at right angles thereto and the intersecting piece extending in the direction of the wearer's legs. The distal end 26 of the intersecting piece is then folded up under the crotch of the wearer in the direction indicated by the arrows in FIG. 2, to the position depicted in FIG. 3. The cross-piece 20 is then folded towards the intersecting piece (see dotted arrows in FIG. 3) until the hooked VELCRO ® strip 16 aligns with one of the loop component strips 17 on the reverse side of the intersecting piece. The cross-piece section is then press-fixed in position. A similar operation is carried out on cross-piece section 19 and this is press-fitted against the distal portion of cross-piece 20 to produce the arrangement shown in FIG. 4.

The final step in the fitting procedure comprises folding the distal end 26 of the intersecting piece back down over the cross-piece so that the VELCRO ® strips 16 and 17 mate. This produces the arrangement shown in FIG. 5.

By extending the VELCRO ® pads to cover relatively large longitudinal sections of the cross-piece and intersecting piece, it is possible to have a garment which is adaptable in size to a wide range of wearers.

Furthermore, the easy press-fix arrangement means that the garment can readily be self-fitted and is particularly suitable for disabled people to fit.

The relatively small amount of material employed in the garment means that it is relatively inexpensive and not unduly bulky or uncomfortable.

Whilst the above has been given by way of illustrative example of the invention, many modifications and variations may be made thereto by persons skilled in the art without departing from the broad scope and ambit of the invention as herein set forth.

What I claim is:

1. An absorbent garment having a cross-piece and an intersecting piece which together form a substantially "T-shaped" configuration when the garment is laid out flat, said cross-piece being a relatively narrow band having opposite ends for encircling the lower trunk of a wearer in an overlapping manner and said intersecting piece being a relatively wider and longer band defining a mid-sectional region and an end region; and said garment including releasable fastening means fitted to said end region, said mid-sectional region and said opposite ends of said intersecting piece and said cross-piece, respectively; whereby, the end region of the intersecting piece passes under the crotch of the wearer and upwardly and then looped over said cross-piece in front of the wearer and fastened to the mid-sectional region to produce a loincloth arrangement.

2. An absorbent garment as claimed in claim 1, wherein the releasable fastening means are hook/loop fasteners.

3. An absorbent garment as claimed in claim 2, wherein a hook component strip is fitted to each end of the cross-piece on one side of the garment and to the free end of the intersecting piece on the other side of the garment, and a loop component mating strip is fitted to one end of the cross-piece on the side opposite to the hook component strips thereon and to the mid-sectional region of the intersecting piece on the same side as the said former loop component, said hook and loop components being located in such a manner as to be in mating alignment when the garment is folded in the shape of a loincloth.

4. An absorbent garment as claimed in claim 1, wherein the region where the two bands meet is enlarged to encompass the entire rear lower portion of the trunk of the wearer, said region being tapered into a relatively narrow section which is adapted to pass under the crotch of the wearer before broadening out to a substantially uniform width of the remainder of its length.

5. An absorbent garment as claimed in claim 4, wherein peripheral edge regions of the relatively narrow section of the garment are elastic.

6. An absorbent garment as claimed in claim 1, further comprising a double layer of absorbent material.

7. An absorbent garment as claimed in claim 6, further comprising an extra layer of absorbent material between the double layers.

* * * * *